(12) United States Patent
Levine

(10) Patent No.: US 8,588,909 B1
(45) Date of Patent: Nov. 19, 2013

(54) TRIGGERED MODE PACING FOR CARDIAC RESYNCHRONIZATION THERAPY

(71) Applicant: Pacesetter, Inc., Sylmar, CA (US)

(72) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/679,191

(22) Filed: Nov. 16, 2012

Related U.S. Application Data

(60) Provisional application No. 61/658,806, filed on Jun. 12, 2012.

(51) Int. Cl.
*A61N 1/00* (2006.01)
(52) U.S. Cl.
USPC .......................................................... 607/14
(58) Field of Classification Search
USPC ................................ 607/14, 4, 9, 25; 600/516
See application file for complete search history.

(56) References Cited

U.S. PATENT DOCUMENTS

| 4,928,688 | A | 5/1990 | Mower |
| 6,466,820 | B1 | 10/2002 | Juran et al. |
| 6,496,730 | B1 | 12/2002 | Kleckner et al. |
| 6,609,028 | B2 | 8/2003 | Struble |
| 2002/0183792 | A1 | 12/2002 | Struble |
| 2006/0224193 | A1* | 10/2006 | Hess .............................. 607/4 |

OTHER PUBLICATIONS

Kurzidim, Klaus et al., "Invasive Optimization of Cardiac Resynchronization Therapy: Role of Sequential Biventricular and Left Ventricular Pacing," PACE. 2005;28:754-761.
Wong, George K. et al., "Ventricular Activation Onset-Triggered Left Ventricular Pacing: Safety and Feasibility in Initial Clinical Experience," PACE. 2004;27 (Pt. I);730-739.

* cited by examiner

*Primary Examiner* — Robert N Wieland

(57) ABSTRACT

A triggered mode pacing system enables dual chamber sensing. The system also determines whether a cardiac event is initially sensed in a first cardiac chamber or a second cardiac chamber. The system then triggers an output to the second cardiac chamber in response to sensing the cardiac event in the first cardiac chamber when the cardiac event was determined to have been initially sensed in the first cardiac chamber.

26 Claims, 8 Drawing Sheets

TRIGGERED MODE PACING FOR CARDIAC RESYNCHRONIZATION THERAPY

CROSS REFERENCE TO RELATED APPLICATION

This application claims the benefit of U.S. Provisional Patent Application Ser. No. 61/658,806, filed Jun. 12, 2012, the disclosure of which is expressly incorporated herein by reference in its entirety.

FIELD

The present disclosure is related, generally, to a method and system for cardiac pacing and sensing, more specifically to a method and system for triggered mode pacing for cardiac resynchronization therapy (CRT).

BACKGROUND

The triggered mode of an implantable medical device (IMD), whether applied to the atrium or the ventricle involves delivery of a pacing stimulus/output in response to a sensed event. After the introduction of dual chamber pacing and sensing, devices with both triggered and inhibited mode functioning at the same time became available. The mode of response to a sensed event in a given chamber (for a triggered and inhibited mode device commonly identified as DDD) is to inhibit the output to the chamber in which the sensed event originated. In response to an event sensed in the atrium, the atrial output is inhibited and an AV delay is initiated. If a ventricular event is not detected within that interval, a ventricular output is triggered in response to the atrial paced or sensed event. This interval is the technologic equivalent of the intrinsic AV nodal conduction interval termed a PR interval when examining the surface electrocardiogram (ECG).

One of the limitations of the first generation of DDD pacemakers was the development of a pathologic atrial tachyarrhythmia that could be tracked by the pacemaker resulting in sustained high rate ventricular pacing. This was first managed by limiting the maximum tracking rate. With the incorporation of rate modulation in DDD pacemakers, manufacturers allowed independent programming of the maximum tracking rate (MTR) and the maximum sensor rate (MSR) where the MSR could be programmed to a rate that was faster than the MTR allowing a higher rate during a physiologic stress such as exercise. The next improvement was the development of a variety of automatic mode switch (AMS) algorithms. These would recognize the pathologic atrial tachyarrhythmia and cause an internal mode switch from a tracking mode (DDD) to a non-tracking mode (VVI or DDI). If there was otherwise intrinsic AV nodal conduction, the pacemaker would be inhibited while the atrial tachyarrhythmia was present. If there was concomitant AV block, the pacemaker would provide ventricular pacing but in a non-tracking mode and hence provide base rate pacing that might be different than the base rate during DDD function or a rate defined by sensor activity (rate modulation). With the introduction of cardiac resynchronization therapy (CRT) where ventricular pacing was specifically desired to provide a more synchronous ventricular activation and contraction pattern, the development of an atrial tachyarrhythmia resulting in AMS, the normal tracking mode reverts to a non-tracking mode, e.g., single chamber, ventricular sensing and pacing in the inhibited mode (VVI) or dual chamber pacing and sensing in the inhibited mode (DDI). This implementation results in inhibition of the ventricular output as long as there is intact conduction resulting in the loss of cardiac resynchronization. Brief episodes of an atrial tachyarrhythmia that are sufficiently rapid to trigger AMS, most commonly atrial fibrillation, have limited adverse effects. However, protracted episodes may significantly compromise the benefits associated with CRT as it functionally disables CRT when AV nodal conduction is intact.

In an effort to address the limitations of prior techniques, manufacturers have introduced the triggered mode to be active during AMS with the desire to maintain the maximal degree of resynchronization possible.

Current generations of high voltage devices generally sense on the right ventricle (RV) channel, although some devices enable left ventricle (LV) signal amplitude measurements. Such left ventricle sensing may be for the purpose of detecting rapid ventricular rates for the potential delivery of anti-tachycardia pacing and/or high voltage therapy. In the original parallel output biventricular (CRT) defibrillators, both the right ventricle and left ventricle activations could be sensed if the second input signal to the sensing circuit occurred after completion of the ventricular refractory period initiated by either the ventricular pacing output or the first sensed component of the ventricular electrogram. This could result in a normal intrinsic or ventricular paced rhythm being interpreted as ventricular tachycardia (VT) or ventricular fibrillation (VF) resulting in the delivery of inappropriate high voltage therapy. As such, most current devices detect only in the right ventricle or in only a single ventricular chamber to eliminate the problem of double counting.

The majority of individuals who receive a CRT system for management of heart failure have a wide intrinsic QRS complex [>120 ms in duration] that is most commonly a left bundle branch block (LBBB) pattern. This means that the earliest intrinsic ventricular activation is on the right side of the heart with the impulse crossing the interventricular septum to begin to activate the left ventricle. This interventricular activation interval is commonly 100 ms or longer. The goal of triggered pacing in a CRT system is to detect intrinsic ventricular activation and then deliver an output pulse as soon after the detected signal as possible to restore some degree of synchronization. In the current generation CRT systems, the output is delivered to both leads which means that output to the RV (because sensing only occurs in the RV) will be wasted as that chamber has already been depolarized. If the signal sensed in the RV originated from the LV, the output pulse to the LV will also be ineffective as that chamber will have already been depolarized.

In addition, many patients with heart failure who would qualify for a CRT system also have frequent premature ventricular complexes (PVCs) which serve to inhibit the pacemaker. The triggered mode could theoretically improve coordination (resynchronization) in association with isolated PVCs. However, if the PVCs arise in the left ventricle as is very common, by the time that it reaches the right ventricle in order to be sensed, both chambers will be fully depolarized and will be refractory to pacing. As such, the triggered mode in this situation is wasting energy without contributing a hemodynamic benefit.

More recent CRT systems have allowed for the independent programmability of left ventricle and right ventricle stimulation and the timing between the two outputs. This allows for adjustment of the inter-ventricular conduction (V-V) interval. In the majority of patients, the general recommendation is for sequential rather than simultaneous pacing with the left ventricle usually stimulated before the right ventricle. With sensing restricted to the right ventricle, delivery of a triggered stimulus to the left ventricle (presuming that the electrical activation also started in the RV) results in right ventricle activation prior to left ventricle activation even if the interventricular conduction delay is minimized.

In patients who have frequent PVCs, particularly arising from the left ventricle as well as a right bundle branch block pattern associated with intrinsic AV nodal conduction, triggered pacing offers little benefit because by the time the intrinsic activation is detected, both chambers will have been depolarized. Therefore, it is desirable to provide a system or method that improves on the current triggered mode technology to help restore CRT in the presence of intrinsic conduction during automatic mode switch or in association with isolated ventricular ectopic beats or PVCs.

Individuals with heart failure and atrial tachyarrhythmias commonly have inter-atrial conduction defects. It has been shown that bi-atrial or dual-site atrial pacing can improve atrial depolarization and reduce the frequency of atrial tachyarrhythmias. At the present time, there are no commercially available pulse generators designed for bi-atrial pacing or four chamber pacing in the presence of concomitant CRT. When there is dual-site atrial pacing; be this two sites in the right atrium or right atrium and left atrium, triggered pacing may also improve both electrical and hemodynamic atrial resynchronization. Similar to CRT in the ventricles, triggered mode pacing may be effective in the atrium in the presence of an intrinsic rhythm such as sinus where the sensed P wave, be this sinus, an ectopic atrial rhythm or isolated atrial premature beats thus improving hemodynamics and reducing the incidence of atrial tachyarrhythmias. Should the patient develop an atrial tachyarrhythmia defined as an atrial rate above a programmed value in pulse per minute or a filtered atrial rate interval shorter than a programmable interval in milliseconds, triggered mode pacing in the atrium will be suspended.

SUMMARY

According to an aspect of the present disclosure a triggered pacing method includes enabling dual chamber sensing. The method also includes determining whether a cardiac event is initially sensed in a first cardiac chamber or a second cardiac chamber. The method further includes triggering an output to the second cardiac chamber in response to initially sensing the cardiac event in the first cardiac chamber.

In another aspect, a triggered mode pacing system has a memory; and at least one processor coupled to the memory. The processor(s) is configured to enable dual chamber sensing. The processor(s) is also configured to determine whether a cardiac event is initially sensed in a first cardiac chamber or a second cardiac chamber. The processor(s) is further configured to trigger an output to the second cardiac chamber in response to initially sensing the cardiac event in the first cardiac chamber.

In still another aspect, a triggered mode pacing system has means for enabling dual chamber sensing. The system also has means for determining whether a cardiac event is initially sensed in a first cardiac chamber or a second cardiac chamber. The system also has means for triggering an output to the second cardiac chamber in response to initially sensing the cardiac event in the first cardiac chamber.

In yet another aspect, a computer program product for triggered mode pacing, comprises a non-transitory computer-readable medium having non-transitory program code recorded thereon. The program code includes program code to enable dual chamber sensing. The program code also includes program code to determine whether a cardiac event is initially sensed in a first cardiac chamber or a second cardiac chamber. The program code further includes program code to trigger an output to the second cardiac chamber in response to initially sensing the cardiac event in the first cardiac chamber.

In another aspect, a triggered mode pacing method includes enabling dual lead sensing in response to detecting an atrial event on a first lead. The method also includes triggering an output to a second lead only in response to sensing the atrial event when a sensed atrial rate exceeds a maximum tracking rate.

This has outlined, rather broadly, the features and technical advantages of the present disclosure in order that the detailed description that follows may be better understood. Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further objects and advantages, will be better understood from the following description when considered in connection with the accompanying FIGURES. It is to be expressly understood, however, that each of the FIGURES is provided for the purpose of illustration and description only and is not intended as a definition of the limits of the present disclosure.

BRIEF DESCRIPTION OF FIGURES

The features, nature, and advantages of the present disclosure will become more apparent from the detailed description set forth below when taken in conjunction with the drawings in which like reference characters identify correspondingly throughout.

DETAILED DESCRIPTION

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion. The following description includes the best mode presently contemplated for practicing the present teachings. The description is not to be taken in a limiting sense but is merely for the purpose of describing the general principles of the illustrative embodiments. The scope of the present teachings should be ascertained with reference to the claims. In the description that follows, like numerals or reference designators will refer to like parts or elements throughout.

Figure 1:
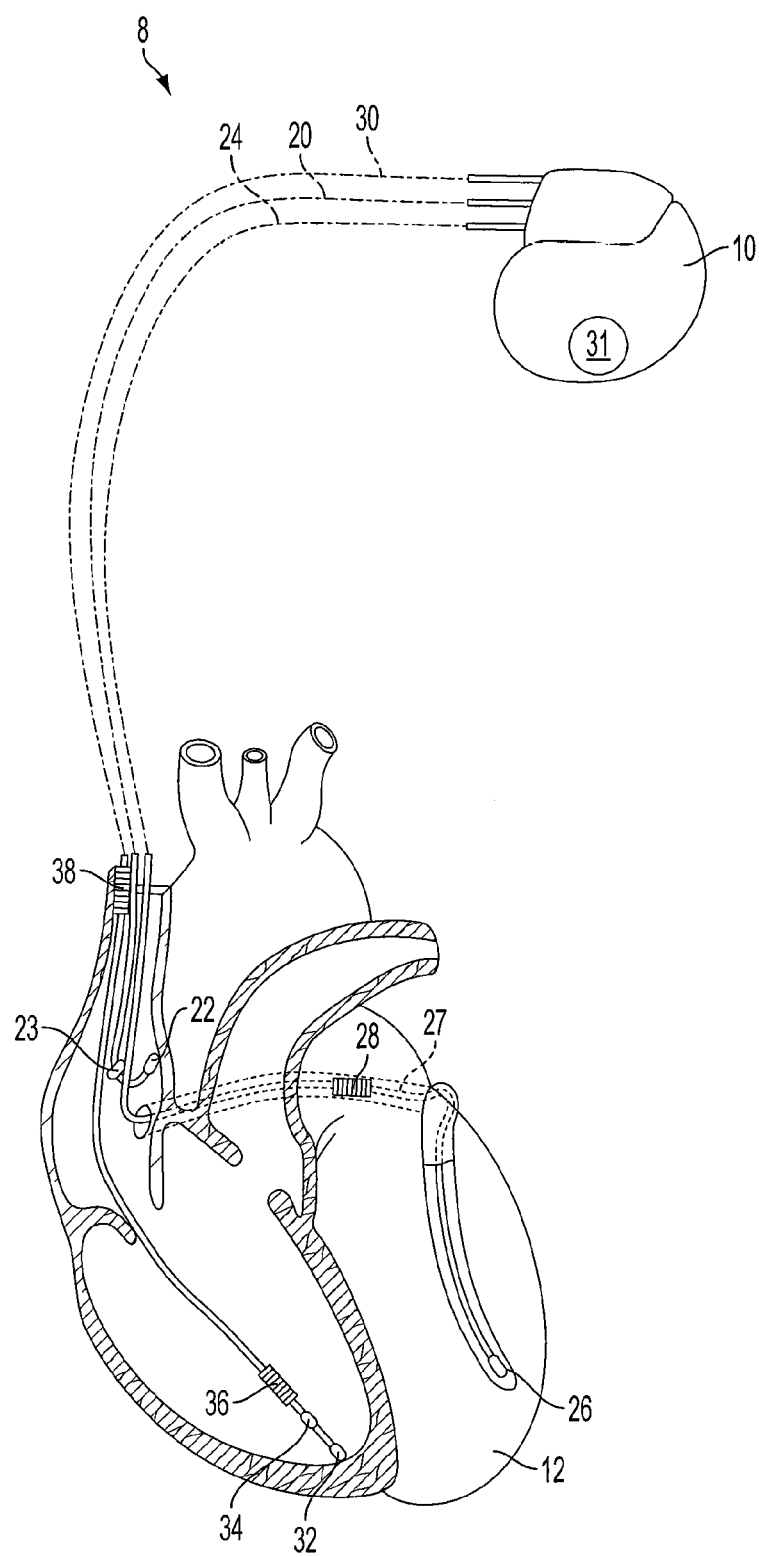
FIG. 1 schematically illustrates an exemplary implantable medical device (IMD) in electrical communication with the heart of a patient.

FIG. 1 schematically illustrates an exemplary implantable medical device (IMD) in electrical communication with the heart of a patient. The medical system 8 includes a pacer/IMD/implantable cardioverter defibrillator (ICD) 10 or other cardiac rhythm management device equipped with one or more cardiac sensing/pacing leads implanted within the heart 12 of the patient. In FIG. 1, a stylized representation of the leads is provided. In some implementations, the pacer/ICD itself performs the optimization based on electrogram signals sensed using the leads. In other implementations, the device transmits features of the electrogram signals to an external device programmer 102 (FIG. 2) that performs the optimization, for example with the QuickOpt algorithm, developed by St. Jude Medical, Inc. That is, the device programmer determines the optimal ventricular pacing parameters, which are then programmed into the pacer/ICD via telemetry. Other external devices can download diagnostic and other data from the implanted pulse generator, such as bedside monitors or the like. In some embodiments, the device programmer or bedside monitor is directly networked with a centralized computing system, such as the HouseCall™ system or the Merlin@home/Merlin.Net systems of St. Jude Medical, Inc.

With reference to FIG. 1, an exemplary implantable medical device (IMD) will be described in detail. The IMD 10 is in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the IMD 10 is coupled to an implantable right atrial lead 20 having at least an atrial tip electrode 22, which typically is implanted in the right atrial appendage, and an atrial ring electrode 23.

To sense left atrial and ventricular cardiac signals and to provide left chamber pacing therapy, the IMD 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior cardiac vein, middle cardiac vein, and/or small cardiac vein or any other cardiac vein accessible by the coronary sinus. Accordingly, an exemplary coronary sinus lead 24 is designed with one or more electrodes to pace and sense from the left ventricle (and can also include a coil for high voltage therapy). In one exemplary configuration, the coronary sinus lead receives atrial and ventricular cardiac signals and delivers left ventricular pacing therapy using at least a left ventricular tip electrode 26, left atrial pacing therapy using at least a left atrial ring electrode 27, and shocking therapy using at least a left atrial coil electrode 28. In another exemplary configuration, a quad polar lead is provided, in which any combination of the four electrodes can be selected or anyone of the electrodes can be selected to operate with the RV coil. Future coronary sinus leads may also include one or more proximal electrodes capable of pacing and/or sensing from the left atrium.

The IMD 10 is also shown in electrical communication with the heart by way of an implantable right ventricular lead (RV lead) 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart so as to place the right ventricular tip electrode 32 in the right ventricular apex so the RV coil electrode 36 is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "vibratory alert" signal (from a motor with an offset mass that can be provided in the device can), an additional electrode can be provided in proximity to the device can. An accelerometer 31 can also be provided to sense three dimensional movements and provide for rate modulation if required for patient management.

Figure 2:
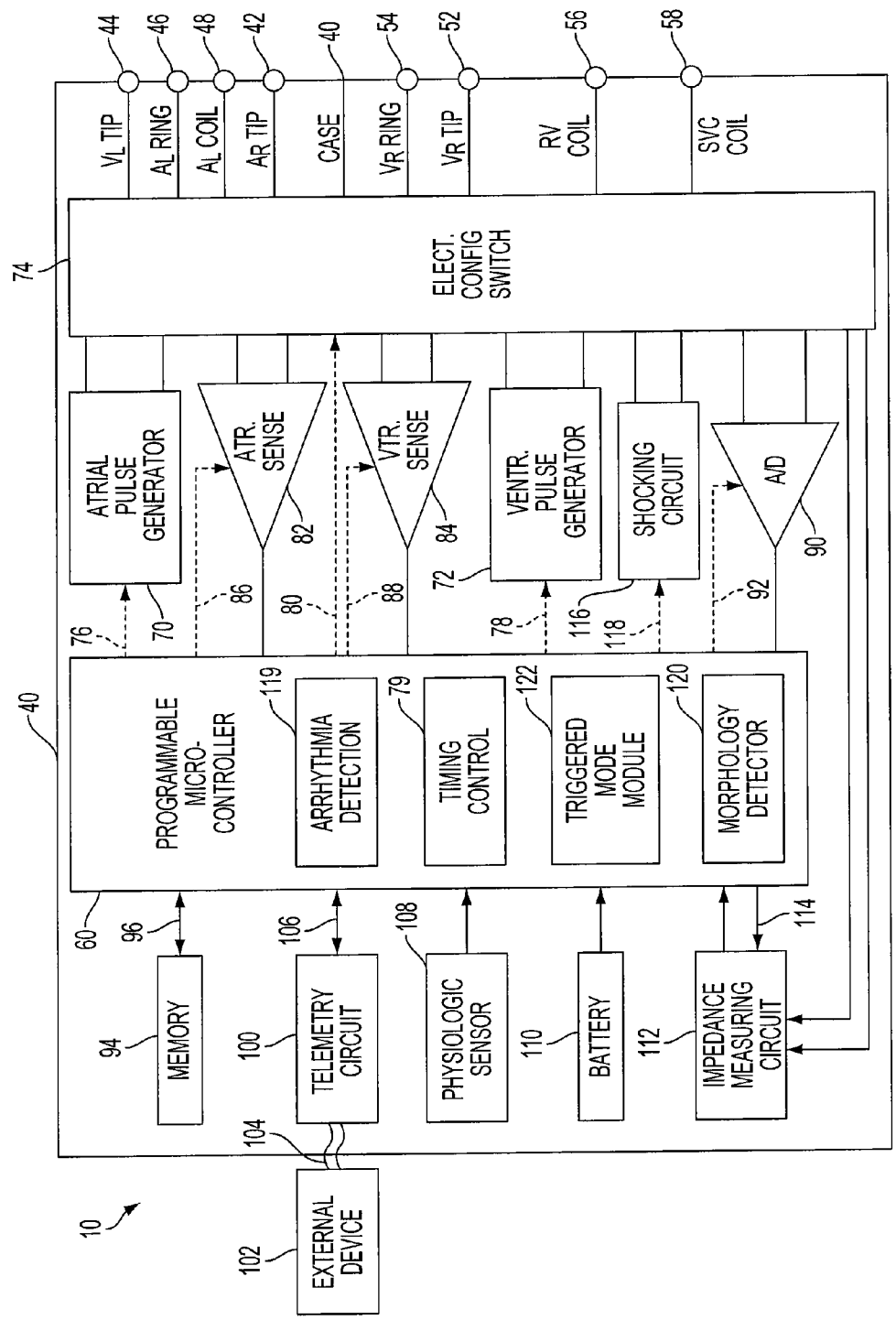
FIG. 2 schematically illustrates an exemplary implantable stimulation device configured as a system according to some aspects of the disclosure.

As illustrated in FIG. 2, a simplified block diagram is shown of the multi-chamber implantable IMD 10, which is capable of treating both fast and slow arrhythmias with stimulation therapy, including cardioversion, defibrillation, and pacing stimulation. The IMD 10 is configured as a system in which the various embodiments of the present teachings may operate. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the IMD 10, shown schematically in FIG. 2, is often referred to as the "housing", "can", "case" or "case electrode" and may be programmably selected to act as the return electrode for a "unipolar" mode. The housing 40 may further be used as a return electrode alone or in combination with one or more of the coil electrodes, 28, 36 and 38, (FIG. 1) for shocking purposes. The housing 40 further includes a connector (not shown) having multiple terminals, 42, 44, 46, 48, 52, 54, 56 and 58 (shown schematically and, for convenience, the names of the electrodes to which they are connected are shown next to the terminals).

As such, to achieve right atrial sensing and pacing, the connector includes at least a right atrial tip terminal (AR TIP) 42 adapted for connection to the atrial tip electrode 22 (FIG. 1) and a right atrial ring (AR RING) electrode (not shown) adapted for connection to the right atrial ring electrode 23 (FIG. 1). To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26 (FIG. 1), the left atrial tip electrode 27 (FIG. 1), and the left atrial coil electrode 28 (FIG. 1), respectively. To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32 (FIG. 1), right ventricular ring electrode 34 (FIG. 1), the RV coil electrode 36 (FIG. 1), and the SVC coil electrode 38 (FIG. 1), respectively. To provide the "vibratory alert" signal, a vibratory alert unit (not shown) generates a signal for an additional terminal (not shown) for connection to the vibratory alert electrode. In one embodiment, the vibratory alert will alert the patient, and then a home monitor can be used to transfer the information associated with the alert from the device 10 to an attending medical professional, who can take the appropriate clinical action.

The IMD 10 includes a programmable microcontroller 60, which controls the various modes of stimulation therapy. As is well known in the art, the microcontroller 60 (also referred to as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of the memory. The details of the design and operation of the microcontroller 60 are not critical to the present teachings. Rather, any suitable microcontroller 60 may be used that carries out the functions described. The use of microprocessor-based control circuits for performing timing and data analysis functions is well known in the art.

As shown in FIG. 2, an atrial pulse generator 70 and a ventricular pulse generator 72 generate pacing stimulation pulses for delivery by the right atrial lead 20 (FIG. 1), the right ventricular lead 30 (FIG. 1), and/or the coronary sinus lead 24 (FIG. 1) via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 that controls the timing of such stimulation pulses (such as pacing rate, atrio-ventricular (AV) delay, atrial interconduction (A-A) delay, or ventricular interconduction (V-V) delay, and the like) as well as to keep track of the timing of refractory periods, blanking intervals, noise detection windows, evoked response windows, alert intervals, marker channel timing, etc., as is well known in the art. A switch 74 includes multiple switches for connecting the desired electrodes to the appropriate I/O circuits, thereby providing complete electrode programmability. Accordingly, the switch 74, in response to a control signal 80 from the microcontroller 60, determines the polarity of the stimulation pulses (such as unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20 (FIG. 1), the coronary sinus lead 24 (FIG. 1), and the right ventricular lead 30 (FIG. 1), through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers and may receive control signals 86, 88 from the controller 60. The switch 74 determines the "sensing polarity" of the cardiac signal by selectively closing the appropriate switches, as is also known in the art. In this way, the clinician may program the sensing polarity independent of the stimulation polarity. Although sensing can be based on a single channel, for example the right ventricle channel, for detection of an event associated with heart failure such as ventricular tachyarrhythmias, sensing can also be implemented on the left ventricle channel. The channel in which sensing occurs can be based on the rhythm of the heart. In some aspects of the disclosure, sensing is implemented on both the left ventricle and the right ventricle channels by incorporating a sense amplifier and/or a sensing circuit on both channels, or any potential combination of electrodes.

Each sensing circuit, 82 and 84, employs one or more low power, precision amplifiers with programmable gain and/or automatic gain control, band pass filtering, and a threshold detection circuit, as known in the art, to selectively sense the cardiac signal of interest. An automatic sensing control enables the device 10 to effectively address the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (for example: P-waves, R-waves, and depolarization signals associated with fibrillation which are sometimes referred to as "F-waves" or "Fib-waves") are then classified by the microcontroller 60 by comparing them to a predefined rate zone limit (for example: bradycardia, normal, low rate VT, high rate VT, and fibrillation rate zones) and various other characteristics (for example: sudden onset, stability, physiologic sensors, and morphology, and the like) in order to determine the type of remedial therapy that is needed (for example: bradycardia pacing, anti-tachycardia pacing, cardioversion shocks or defibrillation shocks, and the like).

Cardiac signals are also applied to the inputs of an analog-to-digital (ND) data acquisition system 90. The data acquisition system 90 is configured to acquire intra-cardiac electrogram (IEGM) signals, convert the raw analog data into a digital signal, and store the digital signals for later processing and/or telemetric transmission to an external device 102. The data acquisition system 90 is coupled to the right atrial lead 20 (FIG. 1), the coronary sinus lead 24 (FIG. 1), and the right ventricular lead 30 (FIG. 1) through the switch 74 to sample cardiac signals across any pair of desired electrodes. The controller 60 controls the data acquisition system via control signals 92. Although FIG. 1 depicts a coronary sinus lead 24, an intrapericardial lead can replace or augment the coronary sinus lead 24.

The microcontroller 60 is further coupled to a memory 94 by a suitable data/address bus 96. The programmable operating parameters used by the microcontroller 60 are stored and modified, as required, in order to customize the operation of the IMD 10 to suit the needs of a particular patient. The microcontroller 60 (or memory 94) includes software modules, such as a triggered mode pacing module 122, which, when executed or used by the microcontroller 60, provide the operational functions of the IMD 10. Additional operating parameters and code stored on the memory 94 define, for example, a pacing pulse amplitude or magnitude, pulse duration, electrode polarity, rate, sensitivity, automatic features, arrhythmia detection criteria, and the amplitude, wave shape and vector of each shocking pulse to be delivered to the patient's heart within each respective tier of therapy. Other pacing parameters include base rate, rest rate and circadian base rate.

Advantageously, the operating parameters of the implantable medical device 10 may be non-invasively programmed into the memory 94 through a telemetry circuit 100 in telemetric communication with the external device 102, such as a programmer, trans-telephonic transceiver, a diagnostic system analyzer, or even a cellular telephone. The telemetry circuit 100 is activated by the microcontroller by a control signal 106. The telemetry circuit 100 advantageously allows intra-cardiac electrograms and status information relating to the operation of the device 10 (as contained in the microcontroller 60 or memory 94) to be sent to the external device 102 through an established communication link 104. In one embodiment, the IMD 10 further includes a physiologic sensor 108, commonly referred to as a "rate-responsive" sensor because it adjusts pacing stimulation rate according to the exercise state of the patient. However, the physiological sensor 108 may further be used to detect changes in cardiac output, changes in the physiological condition of the heart, or diurnal changes in activity (for example, detecting sleep and wake states). Accordingly, the microcontroller 60 responds by adjusting the various pacing parameters (such as rate, AV Delay, V-V Delay, and others) at which the atrial and ventricular pulse generators, 70 and 72, generate stimulation pulses. While shown as being included within the IMD 10, it is to be understood that the physiologic sensor 108 may also be external to the IMD 10, yet still be implanted within or carried by the patient.

The IMD 10 additionally includes a battery 110, which provides operating power to all of the circuits shown in FIG. 2. For the IMD 10, which employs shocking therapy, the battery 110 is capable of operating at low current drains for long periods of time, and is capable of providing high-voltage pulses (for example, for capacitor charging) when the patient requires a shock pulse. The battery 110 also has a predictable discharge characteristic so that elective replacement time can be detected. As further shown in FIG. 2, the device 10 has an impedance measuring circuit 112 enabled by the microcontroller 60 via a control signal 114.

The IMD 10 detects the occurrence of a tachyarrhythmia and if it is ventricular tachycardia, automatically applies an appropriate therapy to the heart aimed at terminating the detected arrhythmia. This could be antitachycardia pacing (ATP) or shock (high voltage) therapy. If the arrhythmia is a supraventricular tachyarrhythmia, mode switch will be engaged if the atrial tachyarrhythmia fulfills predefined programmable criteria. If the ventricular rate is also rapid, the device will determine if it is part of the supraventricular tachycardia at which time ventricular antitachycardia pacing and/or high voltage therapy will be withheld. If the rapid ventricular rate is determined to be independent of the rapid atrial rate and represents a primary ventricular tachyarrhythmia, the microcontroller 60 further controls a shocking circuit 116 by way of a control signal 118. The shocking circuit 116 generates shocking pulses of low (up to 0.5 joules), moderate (0.5-10 joules), or high energy (11 to 40 or more joules), as controlled by the microcontroller 60. Such shocking pulses are applied to the heart 12 through at least two shocking electrodes, and as shown in this embodiment, selected from the left atrial coil electrode 28 (FIG. 1), the RV coil electrode 36 (FIG. 1), and/or the SVC coil electrode 38 (FIG. 1). As noted above, the housing 40 may function as an active electrode in combination with the RV coil electrode 36 (FIG. 1), or as part of a split electrical vector using the SVC coil electrode 38 (FIG. 1) or the left atrial coil electrode 28 (FIG. 1) (for example, by using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (such as corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The microcontroller 60 includes a morphology detector 120 for tracking various morphological features within electrical cardiac signals, including intervals between polarization events, elevations between polarization events, durations of polarization events and amplitudes of polarization events. The microcontroller 60 also includes an arrhythmia detection control 119 that analyzes the sensed electrical signals to determine whether arrhythmia is being experienced. A triggered mode pacing module 122, in cooperation with the memory 94, assists in providing triggered mode pacing to a patient or user.

The remaining FIGURES, flow charts, graphs and other diagrams illustrate the operation and novel features of the IMD 10 as configured in accordance with exemplary embodiments of the present teachings. In the flow chart, the various process steps are summarized in individual "blocks." Such blocks describe specific actions or decisions made or carried out as the process proceeds. Where a microcontroller (or equivalent) is employed, the flow chart provides the basis for triggered mode pacing that may be used by such a microcontroller (or equivalent IMD controller) to adaptively control sensing and pacing. Those skilled in the art may readily write such a program based on the flow chart and other descriptions presented herein.

Figure 3:
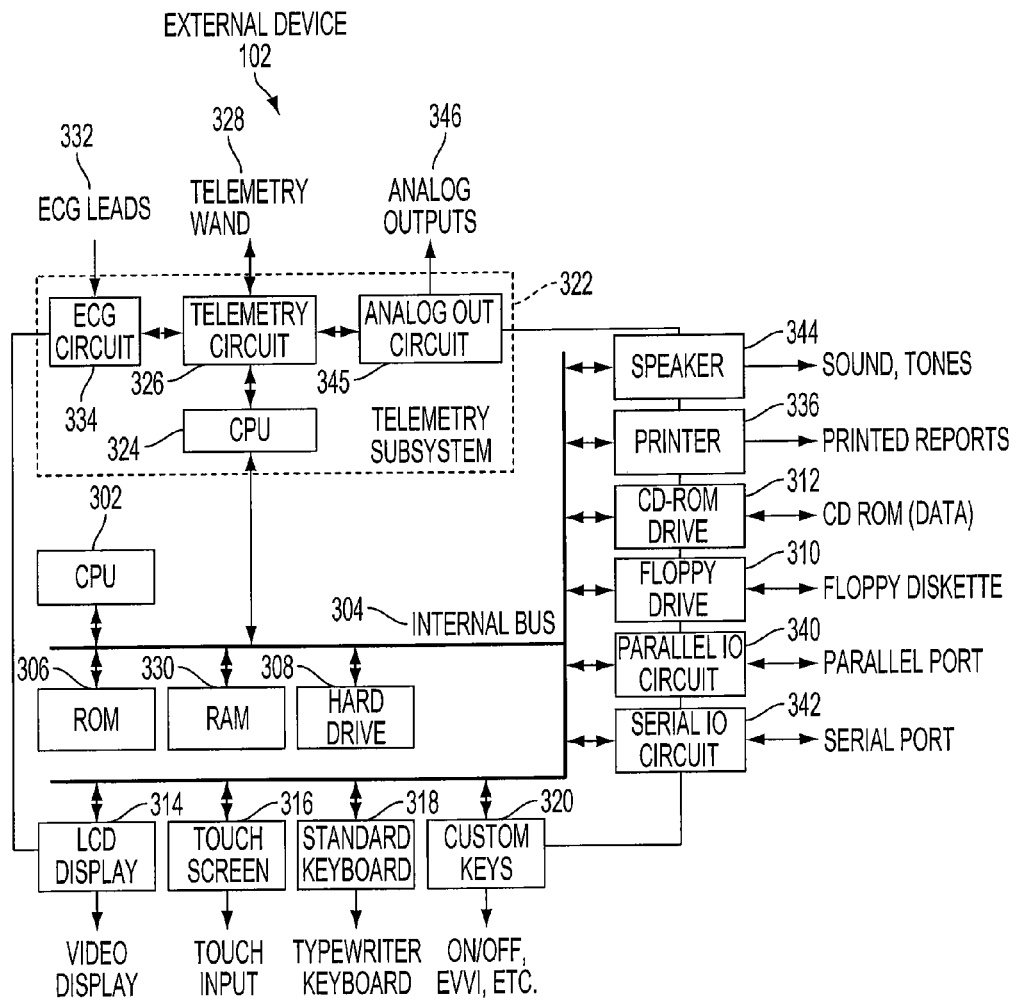
FIG. 3 schematically illustrates an exemplary external device coupled to the implantable stimulation device of FIG. 2.

FIG. 3 schematically illustrates an exemplary external device coupled to the implantable stimulation device of FIG. 2. FIG. 3 illustrates pertinent components of an external device 102 for use in programming the IMD 10 of FIG. 2 and for performing the techniques described herein. Generally, the programmer, physician or other user programs the operation of the IMD 10 to retrieve and display information received from the IMD 10 such as EGM data and device diagnostic data. Additionally, the programmer interface or external device 102 can be optionally equipped to receive and display electrocardiogram (ECG or EKG) data from separate external ECG leads 332 that may be attached to the patient. Depending upon the specific programming, the external device 102 may also be capable of processing and analyzing data received from the IMD 10 and from the ECG leads 332 to, for example, render preliminary diagnosis as to medical conditions of the patient or to the operations of the implanted device.

Now, considering the components of the external device 102, operations of the external device 102 are controlled by a central processing unit (CPU) 302, which may be a generally programmable microprocessor or microcontroller or may be a dedicated processing device such as an application specific integrated circuit (ASIC) or the like. Software instructions to be performed by the CPU 302 are accessed via an internal bus 304 from a read only memory (ROM) 306 and random access memory 330. Additional software may be accessed from a hard drive 308, floppy drive 310, and DVD/compact disc read only memory (CD ROM) drive 312, or other suitable permanent mass storage device. Depending upon the specific implementation, a basic input output system (BIOS) is retrieved from the ROM drive 312 by the CPU 302 at power up. Based upon instructions provided in the BIOS, the CPU 302 "boots up" the overall system in accordance with well-established computer processing techniques.

Once operating, the CPU 302 displays a menu of programming options to the user via an LCD display 314 or other suitable computer display device. To this end, the CPU 302 may, for example, display a menu of specific programmable parameters of the IMD 10 to be programmed or may display a menu of types of diagnostic data to be retrieved and displayed. In response, the physician enters various commands via either a touch screen 316 overlaid on the liquid crystal display (LCD) display 314 or through a standard keyboard 318 supplemented by additional custom keys 320, such as an emergency VVI (EWI) key. The EWI key sets the IMD 10 to a safe VVI mode with high pacing outputs. This may ensure life sustaining pacing operation in nearly all situations but by no means is it desirable to leave the IMD 10 in the EVVI mode at all times.

Once all pacing leads are mounted and the pacing device is implanted, the various parameters are programmed. Typically, the physician initially controls the external device to retrieve data stored within any implanted medical devices 10 and to also retrieve ECG data from the ECG leads 332, if any, coupled to the patient. To this end, the CPU 302 transmits appropriate signals to a telemetry subsystem 322, which provides components for directly interfacing with the implanted medical devices, and the ECG leads 332. The telemetry subsystem 322 includes its own separate CPU 324 for coordinating the operations of the telemetry subsystem 322. The main CPU 302 of the external device 102 communicates with the telemetry subsystem CPU 324 via the internal bus 304. The telemetry subsystem 322 additionally includes a telemetry circuit 326 coupled to a telemetry wand 328, which, in turn, receives and transmits signals electromagnetically from a telemetry unit of the IMD 10. The telemetry wand 328 is placed over the chest of the patient near the IMD 10 to permit reliable transmission of data between the telemetry wand 328 and the IMD 10. Herein, the telemetry subsystem is shown as also including an ECG circuit 334 for receiving surface ECG signals from a surface ECG system having ECG leads 332. In other implementations, the ECG circuit 334 is not regarded as a portion of the telemetry subsystem 322 but is regarded as a separate component.

Typically, at the beginning of the programming session, the external programming device 102 controls the implanted medical devices 10 via appropriate signals generated by the telemetry wand 328 to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the IMD 10 such as lead impedances, battery voltages, battery recommended replacement time (RRT) information and the like. Data retrieved from the IMD 10 also includes the data stored within the recalibration database of the IMD 10 (assuming the pacer/ICD is equipped to store that data.) Data retrieved from the implanted medical devices 10 is stored by the external device 102 either within a random access memory (RAM) 330, hard drive 308 or within a floppy diskette placed within the floppy drive 310. Additionally, or in the alternative, data may be permanently or semi-permanently stored within a DVD, compact disk (CD) or other digital media disk, if the overall system is configured with a drive for recording data onto digital media disks, such as a write once read many (WORM) drive.

Once all patient and device diagnostic data previously stored within the implanted medical devices 10 is transferred to the external device 102, the implanted medical devices 10 may be further controlled to transmit additional data in real time as it is detected by the implanted medical devices 10, such as additional IEGM data, lead impedance data, and the like. Additionally, or in the alternative, the telemetry subsystem 322 receives ECG signals from the ECG leads 332 via an ECG processing circuit 334. As with data retrieved from the implanted medical device 10, signals received from the ECG leads 332 are stored within one or more of the storage devices of the external device 102. Typically, ECG leads output analog electrical signals representative of the ECG. Accordingly, the ECG circuit 334 includes analog to digital conversion circuitry for converting the signals to digital data appropriate for further processing within the external device 102. Depending upon the implementation, the ECG circuit 334 may be configured to convert the analog signals into event record data for ease of processing along with the event record data retrieved from the implanted device. Typically, signals received from the ECG leads 332 are received and processed in real time.

Thus, the external device 102 receives data both from the implanted medical devices 10 and from optional external ECG leads 332. Data retrieved from the implanted medical devices 10 includes parameters representative of the current programming state of the implanted medical devices 10. Under the control of the physician, the external device 102 displays the current programmable parameters and permits the physician to reprogram the parameters. To this end, the physician enters appropriate commands via any of the aforementioned input devices and, under control of CPU 302, the programming commands are converted to specific programmable parameters for transmission to the implanted medical devices 10 via telemetry wand 328 to thereby reprogram the implanted medical devices 10. Prior to reprogramming specific parameters, the physician may control the external device 102 to display any or all of the data retrieved from the implanted medical devices 10 or from the ECG leads 332, including displays of ECGs, IEGMs, and statistical patient information. Any or all of the information displayed by the external device 102 may also be printed using a printer 336.

The CPU 302 can operate to analyze data received from the pacer/ICD, such as LV-IEGM and RV-IEGM data, and to determine optimal or preferred VV pacing delays for use in biventricular pacing or to determine the optimal ventricular chamber for use in monoventricular pacing. Pacing delay parameters and/or other pacing control information may then be transmitted to the IMD 10 to program the device to perform pacing in accordance with the optimal or preferred VV pacing delays or in accordance with monoventricular pacing control parameters.

The external device 102 can also include a modem (not shown) to permit direct transmission of data to other external devices via a public switched telephone network (PSTN) or other interconnection line, such as a T1 line, fiber optic cable or even wirelessly. Depending upon the implementation, the modem may be coupled to the internal bus 304 and/or may be coupled to the internal bus 304 via either a parallel port 340 or a serial port 342. Other peripheral devices may be coupled to the external device 102 via the parallel port 340 or the serial port 342 as well. Although one of each is shown, multiple input output (IO) ports might be provided, including other types of ports, such as USB ports. A speaker 344 can be included for providing audible tones to the user, such as a warning beep in the event improper input is provided by the physician. The telemetry subsystem 322 additionally includes an analog output circuit 345 for controlling the transmission of analog output signals 346, such as IEGM signals output to an ECG machine or a chart recorder.

With the external device configured as shown, a physician or other user operating the external programmer is capable of retrieving, processing and displaying a wide range of information received from the implanted medical devices 10 and to reprogram the implanted medical device 10 if needed. The descriptions provided herein with respect to FIG. 3 are intended merely to provide an overview of the operation of the external device 102 and are not intended to describe in detail every feature of the hardware and software of the external device 102 and is not intended to provide an exhaustive list of the functions performed by the external device.

Figure 4:
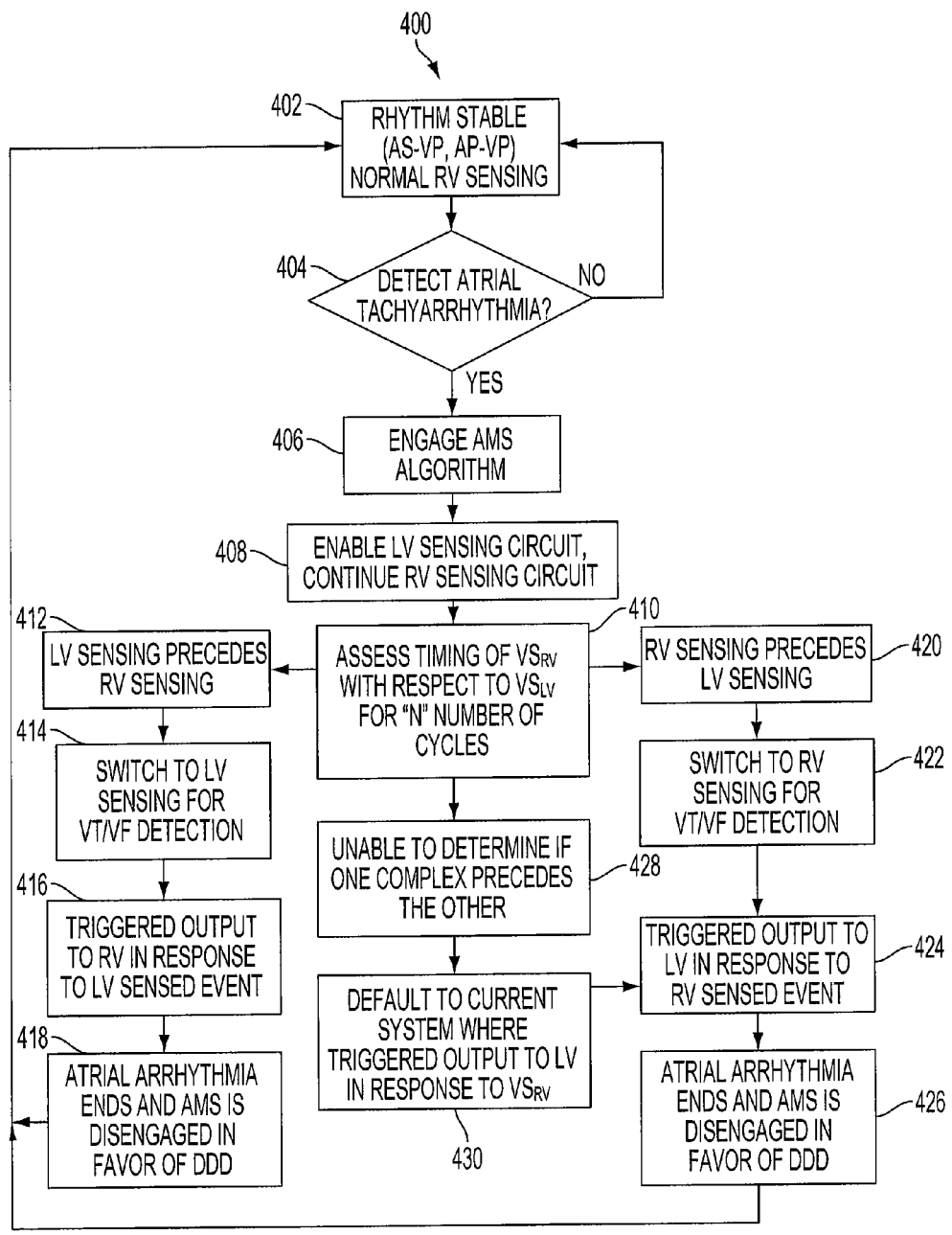
FIG. 4 is a flow diagram of a triggered mode pacing system illustrating an automatic mode switch implementation according to an aspect of the disclosure.

FIG. 4 is a flow diagram of a triggered mode pacing process during automatic mode switch implementation according to aspects of the disclosure. This implementation may also be referred to as a non-tracking mode implementation because there is no tracking of the atrial signals. The atrial signals continue to be monitored to allow a return to the tracking mode when the pathologic arrhythmia ends and the atrial rates return to the normal range. In some aspects of the disclosure, separate sensing circuits, e.g., the right ventricle sensing circuit and the left ventricle sensing circuit, are implemented on each chamber or channel of the heart to sense cardiac events. The right ventricle sensing circuit and the left ventricle sensing circuit may be similar to the sensing circuit 84 described above.

In normal operation, as illustrated in block 402, the heart operates with a normal rhythm and the sensing occurs on the right ventricular channel of the pulse generator. For example, operation during the normal or stable rhythm includes atrial and ventricular pacing (AP-VP) and atrial sensing and ventricular pacing (AS-VP). In some aspects of the disclosure, normal rhythm sensing can occur in the left ventricle. Although sensing can occur in either the right ventricle or left ventricle, the following description assumes sensing based in the right ventricle.

At block 404, it is determined whether an event, e.g., atrial tachyarrhythmia, has been detected. Atrial tachyarrhythmia is a general term referring to any pathologic fast atrial rhythm including an organized atrial tachycardia, atrial flutter, atrial fibrillation, multifocal atrial tachycardia, etc. Atrial tachyarrhythmia could even be sinus tachycardia as well as frequent atrial premature beats, which could also trigger AMS depending on the programmed atrial tachycardia detection rate. After the event is detected, the process continues to block 406 where an automatic mode switching (AMS) algorithm (i.e., not tracking the atria) is enabled. Otherwise, the process returns to block 402 for normal operation.

At block 408, after automatic mode switching is engaged, for a preset number of cycles, the left ventricle sense amplifier or circuit, e.g., sensing circuit 84, is enabled if AV nodal conduction is intact such that there is ventricular sensing. If there is an AV block such that ventricular pacing continues at the mode-switch base rate or the sensor-defined rate, the left ventricular sensing circuit is not activated. With ventricular sensing and activation of the left ventricle sensing circuit, the system can sense from both the left ventricle while right ventricle continues to sense from the right ventricle sensing circuit. At block 410 the system determines which channel detects a cardiac event first. This determination can be made by assessing the time the event was sensed in one chamber, e.g., right ventricle $VS_{RV}$, relative to the time the event was sensed in the other chamber, e.g., left ventricle $VS_{LV}$ with respect to a fixed event, such as an atrial sensed event. The timing of the event can be assessed over a predetermined number (N) of cycles. The channel in which sensing occurs first becomes the sensing channel for purposes of triggered mode pacing and for diagnosing ventricular tachyarrhythmias, such as of ventricular tachyarrhythmias (VT) and ventricular fibrillation (VF).

If the sensing at the left ventricle $VS_{LV}$ precedes the sensing at the right ventricle $VS_{RV}$, thereby indicating the native cardiac event originated at the left ventricle, the process continues to block 412. As a result, the sensing associated with the detection of an event, e.g., ventricular tachycardia (VT) or ventricular fibrillation (VF), is switched to the left ventricle sensing at block 414. In response to a left ventricle sensed event, an output signal is triggered from the IMD 10 to the right ventricle at block 416. That is, triggered mode pacing is based on sensing at the left ventricle. At block 418, the first detected cardiac event, e.g., atrial tachyarrhythmia, subsides and the automatic mode switching algorithm is disengaged in favor of DDD (dual chamber pace, dual chamber sense, dual mode) operation. The process then returns to block 402 for normal operation.

If the sensing at the right ventricle $VS_{RV}$ precedes the sensing at the left ventricle $VS_{LV}$, thereby indicating the ventricular event originated at the right ventricle, the process continues to block 420. As a result, the sensing for diagnosing ventricular tachycardia (VT) or ventricular fibrillation (VF) is from the right ventricle (block 422). Moreover, in response to a right ventricle sensed event, an output signal is triggered from the IMD 10 to the left ventricle at block 424. At block 426, when the first detected cardiac event, e.g., atrial tachyarrhythmia, subsides the automatic switching mode algorithm is disengaged in favor of DDD operation. The process then returns to block 402 for normal operation.

When assessing the timing at block 410, if the system is unable to determine the channel or chamber, i.e., left ventricle or the right ventricle, in which the event was first sensed (block 428), the process continues to block 430. At block 430, the system defaults to a standard operation of triggering a signal output to the left ventricle in response to sensing at the right ventricle. As a result, the process continues to block 424 and so on as already described.

Figure 5:
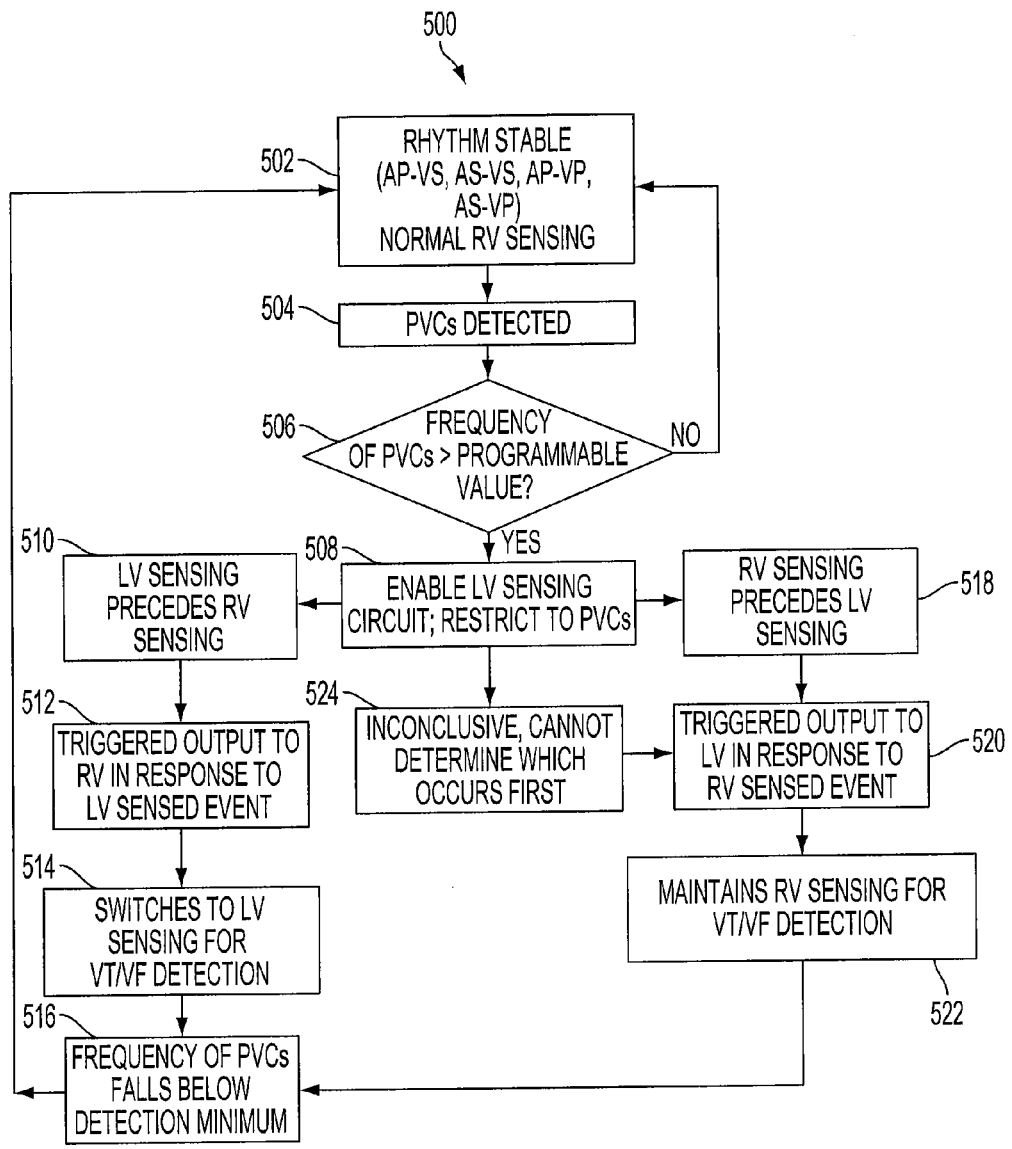
FIG. 5 is a flow diagram of a triggered mode pacing system illustrating triggered response to unifocal premature ventricular complexes (PVCs) according to an aspect of the disclosure.

FIG. 5 is a flow diagram of a triggered mode pacing process in response to unifocal premature ventricular complexes (PVCs). In operation, as illustrated in block 502, the heart operates with a normal or stable rhythm and the sensing occurs at the right ventricle. Operation during the normal or stable rhythm includes, for example, atrial and ventricular pacing (AP-VP), atrial pacing and ventricular sensing (AP-VS), atrial sensing and ventricular sensing (AS-VS) and atrial sensing and ventricular pacing (AS-VP). In some aspects of the disclosure, normal rhythm sensing can occur in the left ventricle, although the following description assumes usual right ventricle sensing.

At block 504, a first cardiac event, e.g., a PVC is detected. A PVC is defined as a sensed ventricular event without preceding atrial activity occurring at 80% or less of the basic sinus cycle length. At block 506, it is determined whether a frequency of the PVCs meets a programmable threshold value. When the frequency of the event (e.g., PVC) fails to meet the threshold value, the process returns to block 502 where the system continues to operate in accordance with a stable rhythm with normal right ventricle sensing. If the rate of detected PVC events is greater than the programmable threshold value, at block 508 the left ventricle sensing circuit is enabled. In some aspects of the disclosure, the left ventricle sensing circuit is enabled and sensing is limited to detecting PVCs, for example employing a morphology discriminator with or without a prematurity index.

The chamber that depolarizes first in association with the PVC becomes the sensing channel upon which triggering of an output is based. For example, if the PVC is detected in the left ventricle before it is detected in the right ventricle (block 510), an output signal is triggered from the IMD 10 to the right ventricle at block 512. At block 514, the left ventricle sensing circuit is used to detect rate and irregularities associated with ventricular tachycardia (VT) or ventricular fibrillation (VF). When the frequency of the event (e.g., unifocal PVC) falls below a detection minimum, block 516, the process returns to block 502 to resume normal operations.

If the PVC is detected in the right ventricle before it is detected in the left ventricle (block 518), then the output is triggered in the left ventricle in response to a PVC being sensed in the right ventricle. At block 522, the right ventricle sensing is maintained to sense irregularities, such as ventricular tachycardia (VT) or ventricular fibrillation (VF). When the frequency of the PVCs falls below a detection minimum (block 516), the process returns to block 502. If it is not clear as to which chamber first detected the PVC (block 524), the process proceeds to block 520.

Figure 6:
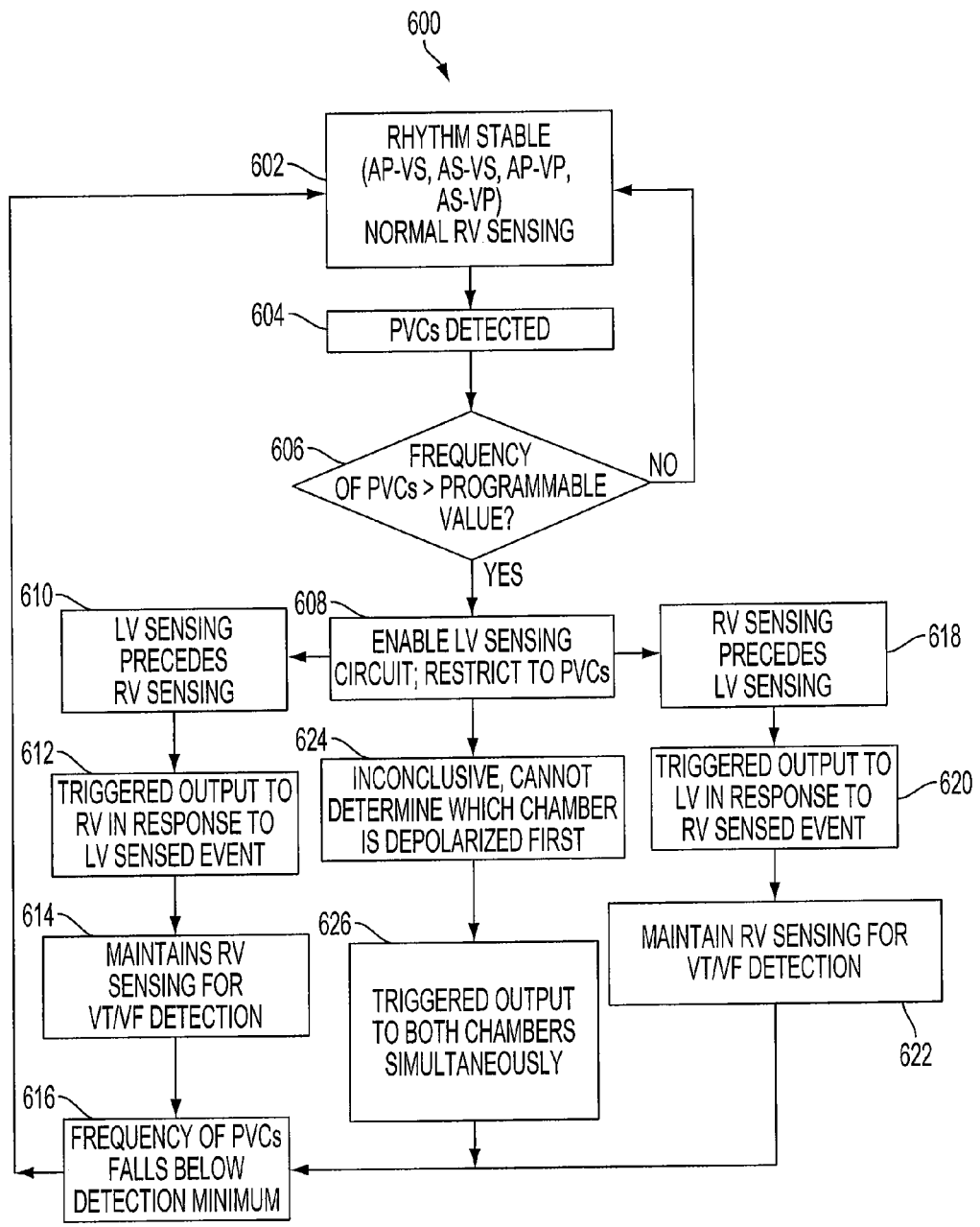
FIG. 6 is a flow diagram of a triggered mode pacing system illustrating triggered response to multifocal premature ventricular complexes (PVCs) according to an aspect of the disclosure.

FIG. 6 is a flow diagram of a triggered mode pacing process in response to multifocal premature ventricular complexes (PVCs) according to aspects of the disclosure. Some patients have multifocal PVCs meaning that the PVCs arise from multiple different sites in one or more chambers. In this situation, both channels remain active and the first detection of a signal triggers an output to the other channel. More specifically, when the basic rhythm of the heart is regular and stable the sensing normally occurs with the right ventricle sensing circuit. However, if frequent PVCs occur, the left ventricle sensing capability is engaged.

In operation, as illustrated in block 602, the heart operates under a normal or stable rhythm and the sensing occurs at the right ventricle sensing circuit. Operation during the normal or stable rhythm includes, for example, atrial and ventricular pacing (AP-VP), atrial pacing and ventricular sensing (AP-VS), atrial sensing ventricular sensing (AS-VS) and atrial sensing and ventricular pacing (AS-VP).

At block 604, an event, e.g., a PVC, is detected. At block 606, it is determined whether a frequency of the event (PVC) meets a programmable threshold value. When the frequency of the event fails to meet the threshold value, the process returns to block 602 where the system continues to operate in accordance with the normal rhythm with normal right ventricle sensing.

When the frequency of the event (e.g., PVC) meets the threshold value, at block 608 a morphology discrimination process is enabled. The morphology discrimination focuses detection on PVCs. Left ventricle sensing also begins at block 608. Similar to the processing described above, although both the left ventricle and right ventricle sensing circuits are enabled, only one of the sensing circuits is used for VF and VT diagnosis.

When the left ventricle sensing of the event precedes the right ventricle sensing of the event (block 610) an output signal is triggered from the IMD 10 to the right ventricle at block 612 in response to sensing an event in the left ventricle. Because the PVCs are multifocal, i.e. originating at multiple different locations, at block 614, the device reverts to right ventricle sensing to diagnose irregularities, such as ventricular tachycardia (VT) or ventricular fibrillation (VF). That is, because the multifocal events cannot be anticipated in advance, the standard detecting resumes. When the frequency of the PVCs falls below a detection minimum (block 616), the process then returns to block 602 to resume normal operations. In another configuration, sensing will continue on both channels but only the first detected event for VT or VF is used. This configuration would allow for almost immediate delivery of a triggered output to the other channel. The sensing of an event in the LV channel would initiate a refractory period in the RV but still allow for delivery of an output pulse to the RV. Similarly, a sensed event in the RV would initiate a refractory period in the LV but still allow for delivery of a triggered output pulse to the LV.

When the right ventricle sensing precedes the left ventricle sensing as illustrated at block 618, an output signal is triggered from the IMD 10 to the left ventricle in response to the right ventricle sensed event, at block 620. At block 622, the right ventricle sensing is maintained to sense irregularities associated with ventricular tachycardia (VT) or ventricular fibrillation (VF). When the frequency of the PVCs falls below a detection minimum (block 616) the process returns to block 602.

After activating left ventricle sensing at block 608, if a determination of the chamber, i.e., left ventricle or the right ventricle, in which the event was first sensed is inconclusive (block 624), the process defaults to normal operation. In other words, the process continues to block 626.

Because it is essential to allow continued diagnosis of ventricular tachycardia (VT) or ventricular fibrillation (VF), controlling sensing/pacing based on location of the PVC (as described with respect to FIGS. 5 and 6) occurs when the basic rhythm of the heart is regular and stable with only periodic interruptions by an early cycle, e.g., PVC. However, if the basic cycle is shorter than the VT detection rate interval, the PVC response can be suspended in an effort to appropriately recognize VT or VF for delivery of anti-tachycardia pacing (ATP) or high voltage therapy. That is, single channel sensing is enabled for diagnostic purposes.

Figure 7:
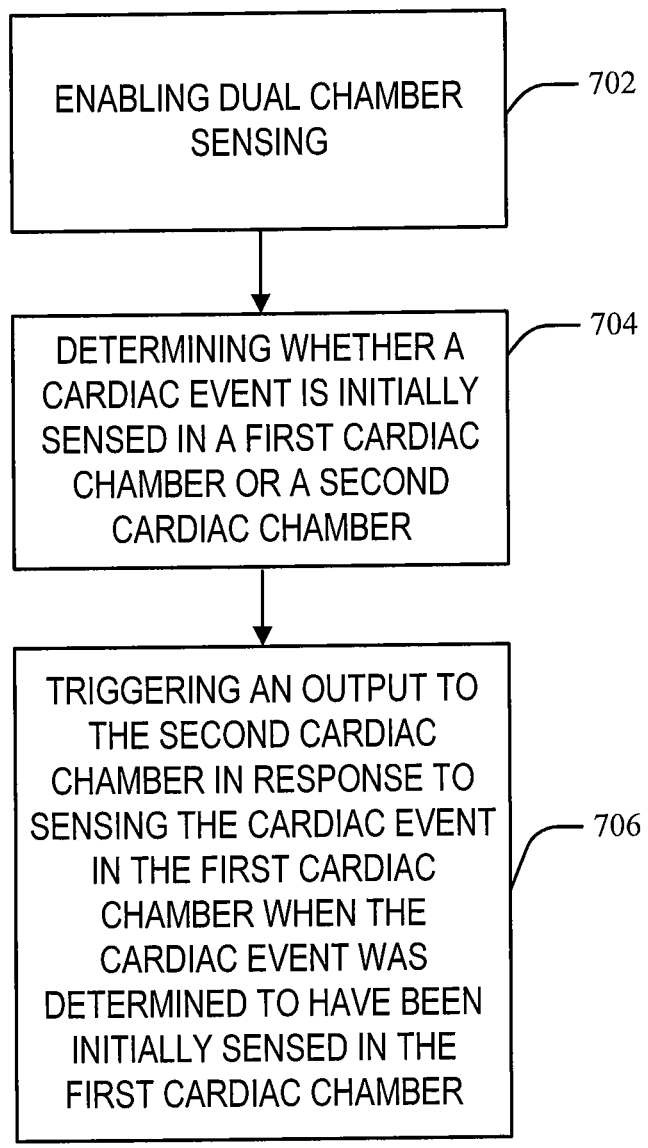
FIG. 7 illustrates a method for triggered mode pacing according to an aspect of the disclosure.

FIG. 7 illustrates a method for triggered mode pacing according to an aspect of the disclosure. At block 702, dual chamber sensing is enabled, for example in response to atrial tachyarrhythmia or premature ventricular contractions (PVCs). At block 704 it is determined whether a cardiac event is initially sensed in the left or right chamber. At block 706, triggered output is based on the chamber that initially sensed the cardiac event. For example, if the cardiac event was initially sensed in the left ventricle, then output to the right ventricle is based on sensing in the left ventricle.

Figure 8:
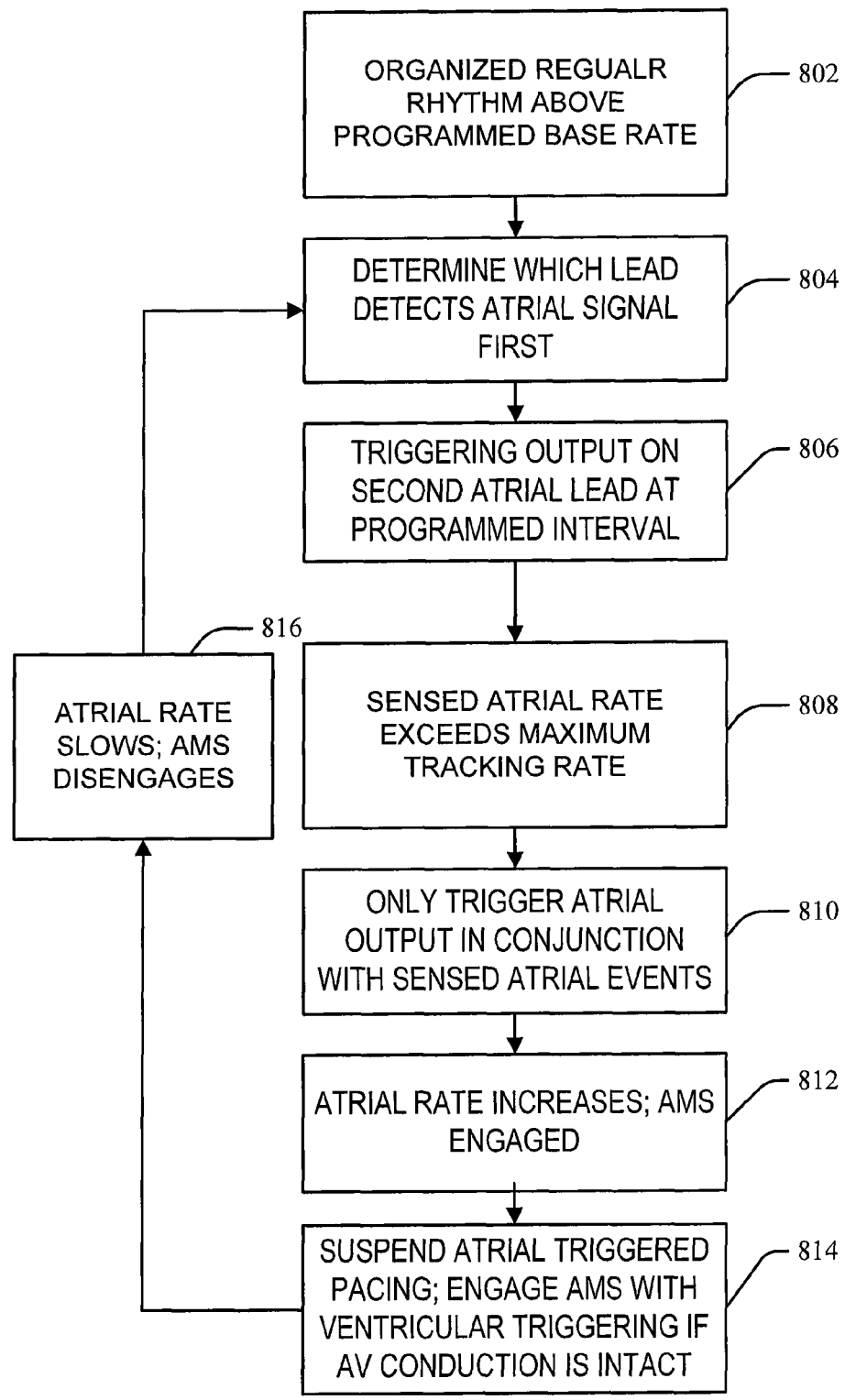
FIG. 8 is a flow diagram for triggered atrial pacing presuming that there are two leads in the atrium, according to an aspect of the disclosure.

FIG. 8 is a flow diagram for triggered atrial pacing presuming that there are two leads in the atrium. If there is a lead in both the right atrium and the left atrium, this would be termed bi-atrial pacing. If there are two leads in one chamber such as high in the right atrial and low in the right atrium, this would technically be termed dual-site atrial pacing. For this discussion, we will use the term "bi-atrial" to refer to either method of multisite atrial pacing. In this example, the rhythm is normal sinus. If the rhythm were marked sinus bradycardia, one could achieve bi-atrial pacing by pacing both chambers at the same time or sequentially at a close coupling interval with one chamber in front of the other depending on where the depolarization occurs first. In the case of sinus rhythm with a lead in the RA and LA, the right atrium will be activated/depolarized first.

At block 802 an organized regular atrial rhythm above the programmed base rate occurs. There is atrial sensing in a system with two leads, either two in the right atrium or one in the right atrium and one in the left atrium. At block 804 it is determined which lead detects the atrial signal first (designated A1). At block 806 output is triggered on a second atrial lead (designated A2) at a programmed interval. The programmed interval could be as soon as the first atrial signal (A1) is detected.

At block 808 the sensed atrial rate exceeds the maximum tacking rate. Thus, at block 810 the atrial output is only triggered in conjunction with the sensed atrial events. At block 812 the atrial rate increases further, such that AMS is engaged. Therefore, at block 814 atrial triggered pacing is suspended. If AV conduction is intact, AMS is then engaged with ventricular triggering. Once the atrial rate slows (block 816), AMS disengages, and the process returns to block 804.

In the setting of frequent Atrial Premature Complexes (APCs), behavior is substantially identical to that described for premature ventricular complexes (PVCs). Unlike ventricular CRT, this can be occurring in the presence of sinus rhythm where the P waves will be tracked, or sinus bradycardia where there will be baseline atrial resynchronization already. Identification of which chamber the APC originates from will be initiated for any atrial sensed event that occurs prematurely defined as X % (e.g. 80%) of the basic pacing cycle length. Then, the system detects which chamber or site the APC originates from. In the setting of an intrinsic atrial sensed rhythm (e.g., sinus) where, for example, sensing occurs first in the RA such that an output is triggered in the LA, if the APC originates from the LA, the system specifically looks during a window up to 80% (or some programmable value) and is capable of delivering the output via the triggered mode to the chamber opposite to that in which the APC originated.

In one configuration, the apparatus includes a means for engaging dual mode sensing; means for determining, and means for triggering. In one aspect of the disclosure, the means may be the implantable medical device 10, the triggered mode module 122, and/or the programmable microcontroller 60 configured to perform the functions recited by the engaging, determining and triggering means. In another configuration, the aforementioned means may be any module or any apparatus configured to perform the functions recited by the aforementioned means.

The present disclosure also applies to a multi-polar lead, such as a quadripolar lead for LV stimulation. In this case, rather than stimulating only two sites (RV and LV), there may be multiple sites of stimulation in both the RV and the LV and there will be multiple potential sites of sensing. Then again, when native ventricular depolarizations are detected, the system learns where the signal is detected first after which it triggers an output to all of the other sites either simultaneously or in a sequential manner, as may be done with the basic system. For example, the RV can be stimulated first followed by LV or LV first followed by RV, and the coupling interval can be controlled. When systems are capable of stimulating at more than two sites, the same will be the case where they will not necessarily stimulate simultaneously but will stimulate sequentially—for example, stimulate site A followed by site C after 10 ms followed by site E after another 20 ms followed by site B after 10 ms more and finally site D 10 ms after that. Then in the triggered mode, the other sites could also be stimulated either simultaneously or in a more sophisticated device, sequentially. The sequence need not be the same as the baseline sequence. Furthermore, the above also applies to the atrium when there is multisite atrial stimulation presuming that intrinsic atrial depolarizations occur.

The methodologies described herein may be implemented by various means depending upon the application. For example, these methodologies may be implemented in hardware, firmware, software, or any combination thereof. For a hardware implementation, the processing units, including programmable microcontroller 60 (FIG. 2) may be implemented within one or more application specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, electronic devices, other electronic units designed to perform the functions described herein, or a combination thereof.

For a firmware and/or software implementation, the methodologies may be implemented with modules (e.g., procedures, functions, and so on) that perform the functions described herein. Any machine or computer readable medium tangibly embodying instructions that may be in a form implantable or coupled to an implantable medical device may be used in implementing the methodologies described herein. For example, software code may be stored in a memory and executed by a processor. When executed by the processor, the executing software code generates the operational environment that implements the various methodologies and functionalities of the different aspects of the teachings presented herein. Memory may be implemented within the processor or external to the processor. As used herein the term "memory" refers to any type of long term, short term, volatile, nonvolatile, or other memory and is not to be limited to any particular type of memory or number of memories, or type of media upon which memory is stored.

The machine or computer readable medium that stores the software code defining the methodologies and functions described herein includes physical computer storage media. A storage medium may be any available medium that can be accessed by the processor of an implantable medical device. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. As used herein, disk and/or disc includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer readable media.

Although the present teachings and its advantages have been described in detail, it should be understood that various changes, substitutions and alterations can be made herein without departing from the spirit and scope of the present teachings as defined by the appended claims. For example, although the preceding description was with respect to the ventricles, the present disclosure is equally applicable to the atrium if multiple site atrial pacing is available. Using triggered mode pacing in the atrium along the same lines as proposed above with respect to PVCs, by synchronizing atrial activity in both chambers in response to an atrial premature complex (APC) may be effective in preventing atrial tachyarrhythmias and also my improve atrial hemodynamics. Similarly, although the preceding description was with respect to a bi-polar lead the concepts equally apply to multi-polar leads, including the quad-polar leads, or even leads with more than four electrodes. That is, the signal origin can be assessed using any and all available electrode pairs to screen for the earliest site of activation and then deliver triggered mode stimulation to the opposite chamber and possibly other electrode pairs within the same chamber but remote from the site of earliest activation. Moreover, the scope of the present application is not intended to be limited to the particular embodiments of the process, machine, manufacture, composition of matter, means, methods and steps described in the specification. As one of ordinary skill in the art will readily appreciate from the disclosure of the present teachings, processes, machines, manufacture, compositions of matter, means, methods, or steps, presently existing or later to be developed that perform substantially the same function or achieve substantially the same result as the corresponding embodiments described herein may be utilized according to the present teachings. Accordingly, the appended claims are intended to include within their scope such processes, machines, manufacture, compositions of matter, means, methods, or steps.

What is claimed is:

1. A triggered mode pacing method, comprising:
enabling dual chamber sensing;
determining whether a cardiac event is initially sensed in a first cardiac chamber or a second cardiac chamber; and
triggering an output to the second cardiac chamber in response to initially sensing the cardiac event in the first cardiac chamber.

2. The method of claim 1, further comprising attempting to diagnose a cardiac irregularity based on sensing from the first cardiac chamber when the cardiac event was determined to have been initially sensed in the first cardiac chamber.

3. The method of claim 1, further comprising attempting to diagnose a cardiac irregularity based on sensing from the first cardiac chamber regardless of whether the cardiac event was determined to have been initially sensed in the first cardiac chamber.

4. The method of claim 1, in which enabling dual chamber sensing occurs when premature ventricular contractions (PVCs) occur a programmable number of times during a predetermined time period.

5. The method of claim 4, further comprising enabling morphology discrimination to limit cardiac event sensing to PVC sensing.

6. The method of claim 4, in which the PVCs comprise unifocal PVCs and the triggering comprises triggering to the a cardiac chamber when it cannot be determined which cardiac chamber first sensed the cardiac event.

7. The method of claim 4, in which the PVCs comprise multifocal PVCs and the triggering comprises triggering to both cardiac chambers substantially simultaneously when it cannot be determined which cardiac chamber first sensed the second cardiac event.

8. The method of claim 1, in which engaging automatic mode switching occurs in response to atrial tachyarrhythmia.

9. The method of claim 8, in which the triggering comprises triggering to a left cardiac chamber in response to sensing the cardiac event in a right ventricle, when it cannot be determined which cardiac chamber first sensed the cardiac event.

10. The method of claim 1, further comprising triggering additional output to a plurality of additional sites.

11. A triggered mode pacing system, comprising:
a memory; and
at least one processor coupled to the memory and configured:
to enable dual chamber sensing;
to determine whether a cardiac event is initially sensed in a first cardiac chamber or a second cardiac chamber; and
to trigger an output to the second cardiac chamber in response to initially sensing the cardiac event in the first cardiac chamber.

12. The system of claim 11, in which the at least one processor is further configured to attempt to diagnose a cardiac irregularity based on sensing from the first cardiac chamber when the cardiac event was determined to have been initially sensed in the first cardiac chamber.

13. The system of claim 11, in which the at least one processor is further configured to attempt to diagnose a cardiac irregularity based on sensing from the first cardiac chamber regardless of whether the cardiac event was determined to have been initially sensed in the first cardiac chamber.

14. The system of claim 11, in which the at least one processor is further configured to enable dual chamber sensing when premature ventricular contractions (PVCs) occur a programmable number of times during a predetermined time period.

15. The system of claim 14, in which the at least one processor is further configured to attempt to enable morphology discrimination to limit cardiac event sensing to PVC sensing.

16. The system of claim 14, in which the PVCs comprise unifocal PVCs and the at least one processor is further configured to trigger by triggering to a left cardiac chamber when it cannot be determined which cardiac chamber first sensed the cardiac event.

17. The system of claim 14, in which the PVCs comprise multifocal PVCs and the at least one processor is further configured to trigger by triggering to both cardiac chambers substantially simultaneously when it cannot be determined which cardiac chamber first sensed the second cardiac event.

18. The system of claim 11, in which the at least one processor is further configured to engage automatic mode switching in response to atrial tachyarrhythmia.

19. The system of claim 18, in which the at least one processor is further configured to trigger by triggering to a left cardiac chamber in response to sensing the cardiac event in a right ventricle, when it cannot be determined which cardiac chamber first sensed the cardiac event.

20. The system of claim 19, in which the at least one processor is further configured to trigger by triggering to the left cardiac chamber in response to sensing the cardiac event in the right ventricle, when it cannot be determined which cardiac chamber first sensed the cardiac event.

21. The system of claim 11, in which the at least one processor is further configured to trigger by triggering additional output to a plurality of additional sites.

22. A triggered mode pacing system, comprising:
means for enabling dual chamber sensing;
means for determining whether a cardiac event is initially sensed in a first cardiac chamber or a second cardiac chamber; and
means for triggering an output to the second cardiac chamber in response to initially sensing the cardiac event in the first cardiac chamber.

23. A computer program product for triggered mode pacing, comprising:
a non-transitory computer-readable medium having non-transitory program code recorded thereon, the program code comprising:
program code to enable dual chamber sensing;
program code to determine whether a cardiac event is initially sensed in a first cardiac chamber or a second cardiac chamber; and
program code to trigger an output to the second cardiac chamber in response to sensing the cardiac event in the first cardiac chamber.

24. A triggered mode pacing method, comprising:
enabling dual lead sensing in response to detecting an atrial event on a first lead; and
triggering an output to a second lead only in response to sensing the atrial event when a sensed atrial rate exceeds a maximum tracking rate.

25. The method of claim 24, further comprising suspending atrial triggered pacing when an automatic mode switch (AMS) occurs.

26. The method of claim 25, in which the AMS is with ventricular triggering when intact atrio-ventricular (AV) conduction exists.

* * * * *